US005858389A

United States Patent [19]
Elsherbini

[11] Patent Number: 5,858,389
[45] Date of Patent: Jan. 12, 1999

[54] SQUALENE IS AN ANTIVIRAL COMPOUND FOR TREATING HEPATITIS C VIRUS CARRIERS

[75] Inventor: Shaker Hamed Elsherbini, Port Reading, N.J.

[73] Assignee: Shaker H. Elsherbini, Port Reading, N.J.

[21] Appl. No.: 980,493

[22] Filed: Dec. 1, 1997

Related U.S. Application Data

[63] Continuation-in-part of Ser. No. 704,089, Aug. 28, 1996, abandoned.

[51] Int. Cl.$^6$ ............................ A61F 13/00; A01N 31/00; A61K 31/045
[52] U.S. Cl. ........................... 424/434; 424/435; 424/439; 424/451; 424/456; 514/739; 514/744; 514/746
[58] Field of Search ................................... 424/478, 434, 424/435, 439, 451, 456; 514/739, 744, 746; 568/843; 570/135

[56] References Cited

U.S. PATENT DOCUMENTS

| 5,503,828 | 4/1996 | Testa et al. | 424/85.7 |
| 5,529,777 | 6/1996 | Andrianov et al. | 424/184.1 |
| 5,554,372 | 9/1996 | Hunter | 424/280.1 |

FOREIGN PATENT DOCUMENTS

| 9701640 | 1/1997 | WIPO . |

OTHER PUBLICATIONS

Purcell, R.H. Hepatitis C Virus; historical perspective and current concepts, *FEMS Microbial Rev.* 14, 181–192, (1994).

Van der Poel, C.L. Hepatitis C Virus. Epidemiology, transmission and prevention. In Hepatitis C Virus. Current Studies in Hematology and Blood Transfusion, H. W. Reesink ed. (Baset: Karger), pp. 137–163, (1994).

Love, R.A., Parge, H.E., Wickersham, J.A. Hostomsky, Z., Moomaw, E.W. and Hostomska, Z. in Agouron Pharmaceuticals, Inc. & Habuka, N. and Adachi, T. in Japan Tobacco, Inc. (Central Pharmaceutical Research Institute) and University of Tsukuba, Japan (Center for Tsukba Advanced Research Alliance). "The Crystal Structure of Hepatitis C Virus NS3 Proteinease Reaveals a Trypsin–like Fold and Structural Zink Binding Site," *Cell,* 87, 331–342, (1996).

Kim, J.L., Morgenstern, K.A., Lin, C., Fox, T., Dwyer, M.D., Landro, J.A., Chambers, S.P., Markland, W., Lepre, C.A. O'Malley, E.T., Harbeson, S.L., Caron, P.R. and Thompson, J.A. in Vertex PHarmaceuticals, Inc. & Rice, C.M. from Washington University, School of Medicin. "Crystal Structure of Hepatitis C Virus NS3 Protease Domain Complexed with Synthetic NS4A Cofactor Peptide." *Cell,* 87, 343–355, (1966).

Alter, M.J., and Maste, E.E. "The Epidemiology of Viral Hepatitis in the United States." *Gastroenterol. Clin. North Am.* 23, 437–455., (1994).

Choo, Q.L., Kuo, G., Weiner, A.J., Overby, L.R., Bradley, D.W. and Houghton, M. "Isolation of cDNA clone derived from blood–borne non–A, non–B viral hepatitis." *Science,* 244, 359–362, (1989).

Iwarson, S. "The natural course of chronic heaptitis," *FEMS Microbial. Rev.* 14, 201–204,(1994).

Alter, H.J., Purcell, R.H., Shih, J.W., Melpolder, J.C., Houghton, M., Choo, Q.L., and Kuo, G. "Detection of antibody to hepatitis C virus in prospectively followed transfusion recipients with acute and chronic non–A, non–B hepatitis." *New Engl. J. Med.* 321, 1494–1500, (1989).

Kuo, G., Choo, Q.L., Alter, H.J., Redeker, A.G., Purcell, R.H., Miyamura,T., Dienstag, J.L., Alter, M.J., Stevens, C.E., et al. "An assay for circulating antibodies to a major etiologic virus of human non–A, non–B hepatitis." *Science* (1989).244, 362–364.

Renault, P.F., and Hoofnagle, J.H. "Side effects of alpha interferon." *Semin. Liver Dis.* 9, 273–277, (1989).

Statistical data from *C&S Clinical Lab. Inc.,* P.O. Box 5269, Englewood, N.J. 07631–5269.

John Gerared, "The Herbal or General History of Plants" the complete 1633 edition is revised and enlarged by Thomas Johnson, *Dover Pulbications Inc.,* NY (copyright 1975).

James Duke, "CRC Handbook of Medicinal Herbs", *CRC Press Inc.* Dated Jul. 24, 1986, Scientific Library Pat TM Office.

Kee Chang Huang, "The Pharmacology of Chinese Herbs", *CRC Press Inc.,* (1993).

Schvarcz R.; Ando, Y., Sonnerborg, A. and Weiland, O.; Combination treatment with interferon alfa–2b and ribavirin for chronic hepatitis C in patients who have failed to achieve sustained response to interferon alone: swedish experience. *J Hepatol.* 1995; 23 (Suppl 2): 17–21.

Van de Waterbeemd, H. "The History of Drug Research: from Hansch to Present." *Quant. Struct.–Act. Relat.* 11: 200–204, (1992).

Van de Waterbeemd, H. "Recent Progress in QSAR–Technology." *Drug Des. Discov.* 9: 227–285, (1993).

Stanon, D.T. Murray, W.J. and Jurs, P.C. "Comparison of QSAR and molecular similarity approaches for a stucture–activity relationships study of DHFR inhibitors." *Quant. Struct.–Act. Relat.* 12: 239–245, (1993).

Woldawer, A. and Erickson, J.W. "Structure–based inhibitors of HIV–1 protease."*Annu. Rev. Biochem.* 62: 543–585, (1993).

(List continued on next page.)

*Primary Examiner*—Leon B. Lankford, Jr.
*Assistant Examiner*—Christopher R. Tate

[57] ABSTRACT

A method and composition for treatment of hepatitis C virus (HCV), administered as two component treatment, involving 1) an orally administered squalene in combination with 2) the inhalation of squalene medication. Each medication component must be administered concurrently.

3 Claims, No Drawings

OTHER PUBLICATIONS

Tute, M.S. History and objectives of quantitative drug design. In Hansch, C., Sammes, P.G. and Taylor, J.B. (eds) *Comperhensive Medicinal Chemistry,* vol. 4, *Quantitative Drug Design,* pp. 1–31. Pergamon Press, New York (1990).

Hansch, C. The physicochemical approach to drug design and discovery (QSAR). *Drug Rev. Res.* 1: 267–309. (1981).

Hansch, C.On the state of QSAR. *Drug Inf.J.* 18:115–122, (1984).

Craig, P.N. QSAR–origins and present status: a historical perspective. *Drug Inf.J.* 18: 123–130, (1984).

Fujita, T. Application of quantitative structure–activity relationships in drug design. *Acta Pharm. Jugosl.* 37: 43–51, (1987).

Tsujimoto et al. Vaccine. vol. 7(1), pp. 39–48, Abstract enclosed, 1989.

SQUALENE IS AN ANTIVIRAL COMPOUND FOR TREATING HEPATITIS C VIRUS CARRIERS

CROSS-REFERENCE TO RELATED APPLICATION

This application is a Continuation-in-part application (CIP) of application Ser. No. 08/704,089, filed Aug. 28, 1996, now abandoned.

BACKGROUND OF THE INVENTION

1. Field of the Invention

The present invention relates to a method and composition for treatment of hepatitis C virus (HCV), administered as a two component treatment, involving 1) an orally administered SQUALENE, 500 mg twice per day and 2) the inhalation of squalene through the nasal membrane to the blood stream three times per day, 2-to-3 drops (10 to 15 mg.) each time. The period of treatment is two to six months, depending on the quantity of the viral load. The two components are administered concurrently to achieve the best results. Medicinal theoretical study have shown that squalene has the potential of antiviral activity, furthermore, in vitro assay has shown that the squalene compound inhibits the replication of hepatitis C virus and competitive to interferon-α(IFN). This is beside the use of that treatment on a hepatitis C patient.

2. Description of Prior Art

Chronic infection by hepatitis C virus (HCV) is a global disease and the number of carriers is estimated to be 300 million (reported by Purcell in 1994, Van der Poel in 1994, Love et al. In 1996 and Kim et al. In 1996). Alter and Maste in 1994 reported that four million individuals are in the United States alone. Outside the United States, for example in Egypt, 25% of the Egyptian population is infected. HCV is the major etiologic agent or human parentally and community-acquired non-A, non-B hepatitis (NANBH) (Choo et al. in 1989). Most HCV infections occur by blood transfer, whether by blood transfusion or a contaminated syringes, which is often seen in cases of shared syringes by drug addicts.

20% of the infected individuals develop acute clinical hepatitis (Kim et, al. in 1996). However, in most cases the virus establishes a chronic infection that persists for decades as stated by Iwarson in 1994. The uncertainty of the availability or even the prospects of safe and effective anti-HCV vaccines, made no protection against HCV for many years. The unavailability of HCV diagnostic identification, until it was recently identified by molecular cloning and sequencing around 1989 (Alter et al., Choo et al., Kuo et al.), where technology of the diagnostic test became available to the diagnostic laboratories and the practicing physicians in early 1990's. Prior to that time, chronic HCV infections could have been asymptotic, therefore, making diagnosis of HCV cases by the physician difficult and essentially undetectable until late stage when secondary effects of the infection are noted by the patient, who only then seeks treatment. Moreover, no reported method exists for effective treatment of late stage HCV carriers, with the exception of interferon (IFN) treatment which have significant side effects (Renault et al. In 1989) or liver transplantation, which has unpredictable results in some cases. Even though, the patients who go for liver transplantation and still have HCV in their blood stream still at risk from developing liver cirrhosis and other complications. At present the only accepted medical treatment is the IFN; its positive response is observed in about 50% of the patients with chronic HCV infection and the reduction in the viral load was averaged to 25 to 31% (Statistical data from C&S clinical Laboratories Inc.). Although IFN has shown great promise in a subset of patients treated for a prolonged period of time, these response rates have overall, unfortunately been disappointing, and toxicity to effective doses is substantial. Therefore, the need for an effective treatment to abolish HCV completely from the patient system is necessary.

Because of latent nature of the symptomatology (10 to 15 years) of the infection, the liver may be saved only if the chronic liver disease is not sufficiently advanced. This can be achieved if the HCV replication can be inhibited by the use of certain anti-HCV compound if available. A proportion of those patients will, nevertheless, ultimately develop problems such as cirrhosis, portal hypertension, varices, gastric erosions, ulcers and hepatocellular carcinoma. With this understanding, it is not surprising that late stage HCV carriers are still at increased risk of morbidity and mortality. A review of the patents and medical literature fails to reveal any suggested safe remedies for HCV. However, there are alternative methods for treatment using natural products which is historically known to cure liver and gastric problems (John Gerared, James Duke, and Kee Chang Huang), however, according to the late clinical trial in Egypt (personal communication), where they used undisclosed group of herbs for the treatment of hepatitis C. The analysis of the herbs used have shown to contains some toxic substances, which in unregulated doses can cause serious side effects and makes the use of these herbs as a treatment for HCV dangerous. Such poison constituents include: Pyrogallol, which when ingested, causes gastrointestinal irritation, renal and hepatic damage, hemolysis, methemoglobinemia, convulsion, circulatory collapse and even death; Camphor, which when ingested or injected causes nausea, vomiting, vertigo, mental confusion, delirium, colonic convulsion, coma, respiratory failure and death; and Bis(2-ethylhexyl)Phthalate where the symptoms of its exposure are irritation of eyes and mucous membranes and may reasonably be anticipated to be carcinogen [Seventh Annual Report on carcinogens (PB95-109781, 1994) p. 168]. Moreover, case studies of HCV treatment using the undisclosed herbs have been released in which symptoms have been reported suggested the above mentioned poison constituents, and thus suggesting the identity of the herbs.

Medicinal information sources shows that, there are many pharmaceutical preparations for viral hepatitis, however none of them is specific for HCV except the IFN. This could be due to at least three reasons. First: because of the late discovery of the HCV diagnostic test. Second: because of the latent nature of the HCV infections. Third: the receptors or reaction sites were not clear until very recently on October of 1996, when two research groups (Love et al.) in Agouron Pharmaceuticals and (Kim et al.) In Vertex Pharmaceuticals published simultaneously their articles about the possible HCV sites which could be the basis for future efforts for drug design. Recently, the combination of Ribavirin and IFN was introduced as a therapy of chronic hepatitis C (Schvarcz et al.) where a clinical trial was made in four European countries showing shorter period of treatment than IFN alone and a sustained response rate defined as normal alanine aminotransferase (ALT) levels and undetectable HCV RNA in six months after the end of therapy.

THE IN VITRO ASSAY METHOD

The in vitro assay method used for testing the antiviral activity of the squalene compound purchased commercially, upon my request, was developed by Prof. El-Awady, the chairman of the molecular biology department in the National Research Center in Egypt. In that assay he employed a novel test to determine the anti HCV efficacy of pure known compounds that are chemically synthesized or isolated from the herbal extracts. The assay is based on a unique feature of flavivirus genome replication where RNA positive strand does not include DNA intermediates but rather replicates through siring a minus (antigenomic strand) using specific RNA dependent RNA polymerase. The feasibility of detecting the minus strand by PCR allows monitoring of intracellular viral replication. Peripheral blood monocular cells (PBMC) of HCV infected individuals is cultured in RPMI 1640 medium containing 10% fetalcalf serum, 100 mg/ml penicillin G, 100 mg/ml streptomycin sulfate, is incubated with phytoheamaglutinin/TBA for 30 hours and then exposed to various concentrations of antiviral compounds for 12 hours. For control experiments commercial antiviral agents Interferon-alpha, virasol e.g. (Mevalonate derivatives) etc. are incubated with mitogen stimulated cells for 24 hours. Total RNA is then extracted from cells and both plus and minus strands are amplified by PCR using strand specific primers. Inhibition or abolishing minus strand synthesis in presence of specific compound denotes anti HCV activity. The assay is very sensitive and reproducible. This Test has shown that the squalene have anti-HCV activity.

SUMMARY OF THE INVENTION

The present invention relates to a method and composition for treatment of hepatitis C virus carriers (HCV), administered as two component treatment, involving 1) an orally administered SQUALENE gel Capsules (500 mg twice per day) in combination with 2) the inhalation of SQUALENE compound 2–3 drops (10 to 15 mg) three times per day

DETAILED DESCRIPTION OF THE PREFERRED EMBODIMENT

1. MEDICINAL CHEMISTRY STUDY OF THE SQUALENE

A medicinal Chemistry study was conducted in which the prediction of anti-HCV compounds is done using appropriate chemical information data management and analysis systems computer-assisted techniques which are widely used to store information in databases in a form of that so-called molecular spread sheets. This is used for structure-activity relationships (SAR) studies. A study aiming at the correlations between intrinsic, physical and chemical or biological molecular properties, structure-property correlation (SPC) (Woldawer et al. In 1993 and Iute in 1990). The study is conducted using software available in the market. These are also called Quantitative Structure-Property Relationships (QSPR.) (Hansch in 1981). When biological properties or activities are involved, Quantitative Structure Activity Relationship (QSAR) forms a subset of this.

Many antiviral compounds for HIV have been developed so far, where the protease sites were known for a long time. The similarity between HIV and HCV is due to that HIV-protease is an essential enzyme for the replication of HIV and is widely regarded as one of the most promising targets for the design of new drugs for the treatment of AIDS. As a result many hundred of inhibitor classes have already been identified and crystal structures have been determined for at least 160 complexes of inhibitors with the enzyme (Hansch in 1984). The HCV molecular site is a protease enzyme also (Love et al. And Kim et al. In 1996). Although they are different proteases, however, using this similarity has benefitted the search for a drug for HCV. If we have a drug candidate, it is

TABLE 1

HIV-protease inhibitor antivirals.

| Antiviral | Molecular Formula | Manufacturer |
|---|---|---|
| 1. Acyclovir | $C_8H_{11}N_5O_3$ | Merck |
| 2. BMS-187071 | $C_{32}H_{49}N_3O_6$ | Bristol Myers Squib |
| 3. BMS-182193 | $C_{30}H_{45}N_3O_6$ | Bristol Myers Squib |
| 4. BMS-186318 | $C_{36}H_{54}N_4O_9$ | Bristol Myers Squib |
| 5. Calanolide A | $C_{22}H_{26}O_5$ | |
| 6. Indinavir | $C_{36}H_{47}N_5O_4$ | Merck |
| 7. KNI-272 | $C_{33}H_{41}N_5O_6S_2$ | Nikko Kyodo Co. |
| 8-KNI-227 | $C_{35}H_{45}N_5O_6S_2$ | Nikko Kyodo Co. |
| 9- Ritonavir | $C_{37}H_{48}N_6O_5S_2$ | Abbott |
| 10- Samquinavir | $C_{38}H_{50}N_6O_5$ | Hoffman Laroche |
| 11-XM-323 | $C_{35}H_{38}N_2O_5$ | Dupont Merck Pharmaceutical |
| 12-Zidovudine (AZT) | $C_{10}H_{13}N_5O_4$ | Burrough Welcome | advantageous to start the molecular modeling with a preliminary structure-property correlation (SPC) studies. Therefore, we have conducted in-depth SPC. study prior to molecular modeling study which helped us finger pointing the compounds which have antiviral activity against HCV.

In the SPC study we used protease inhibitor anti-HIV drugs for correlation with some chosen squalene isomers as anti-HCV of drug molecules. The anti-HIV drugs used are:

| [1] Acyclovir, | [2] BMS-187071, | [3] BMS-182193, |
|---|---|---|
| [4] BMS-186318, | [5] Calanolide A, | [6] Indinavir, |
| [7] KNI-272, | [8] KNI-227, | [9] Ritonavir, |
| [10] Samquinavir, | [11] XM-323, | [12] Zidovudine(AZT). |

Where BMS refers to Bristol Myers Squib Co. and associated numbers are code numbers made by the company. KNI refers to Kyodo Nikko Co. And XM-323 is an antiviral made by Dupont-Merck Pharmaceutical.

TABLE 2

The Computer Printout of the Press Test.

Compounds with highest predicted values:

| sq11 | (8.411494) | cis-cis squalene |
|---|---|---|
| sq21 | (8.394141) | trans-cis squalene |
| sq22 | (8.392908) | trans-trans squalene |
| sq12 | (8.375626) | cis-trans squalene |
| sq31 | (7.488726) | 2-aza-2,3-dihydrosqualene, antifungal |
| BM +51.0836 | (7.187380) | antiviral; inhibits HIV-1 reverse transcriptase made by Bohringer Mannheim. |
| L-702019 | (6.773015) | antiviral; inhibitor of HIV-1 reverse transcriptase, made by Merck. |
| sq32 | (6.632001) | 2-aza-2,3-dihydrosqualene HCl, antifungal |
| S-2720 | (6.263846) | antiviral inhibits HIV-1 reverse transcriptase and replication, made by Hoescht. |
| thiazolobenzimidazole (TBZ) | (5.999923) | antiviral; inhibits HIV-1, also known as NSC 625487. |
| sulfoxamine | (5.619261) | antiviral; inhibits HIV-1, also known as NSC 287474. |
| R86183 | (5.445646) | antiviral; HIV-1, replication inhibitor; synergistic with |

TABLE 2-continued

The Computer Printout of the Press Test.

Compounds with highest predicted values:

|  |  | 2',3'-dideoxynucleoside analogs, made by Janssen. |
|---|---|---|
| Cl-TIBO (R82913) | (5.444047) | antiviral; inhibits HIV-1 reverse transcriptase, made by Janssen. |
| NPPS | (5.304927) | antiviral; inhibits HIV-1 reverse transcriptase, $C_{12}H_9NSO_4$. |

Our isomers of squalene, which are sq11, sq12, sq21, and sq22 refers to cis-cis, cis-trans, trans-cis and trans-trans squalene respectively, which will be refered to as SQxx.

As we know that Log P is the predominant descriptor in many structure-property correlation studies which is a function of the penetration of the drug molecule through the cell membrane. The Log P values of our SQxx series of the squalene isomers are significantly higher than that of HIV-protease inhibitors used in the study. Other similar SPR studies are conducted using other variables as percent of hydrophilic surface, molecular volume, surface area, solubility parameter density, vapor pressure, molar refraction {MR=MW*[index of refraction-1]/[density squared* (index of refraction+2)] for liquids}, and water solubility. These intrinsic and physico-chemical properties are functions of biological properties of drug molecules. All these correlation studies were done using multiple linear regression analysis (MLR) showing similar results of the superiority of squalene over the other known antiviral compounds. We do not know if SQxx series is itself the HCV-protease inhibitor or one of its metabolites or by-products, which could be further investigated, however it is a good start as lead compounds. A printout of the contribution to PRESS (Predictive Residual Sum of Squares) is listed in Table 2.,which shows that squalene is on the top of the list due to its high Log P value. A number of reviews have documented the history, strategy and success of quantitative drug design, i.e. design using SPC/QSAR methods (Van de Waterbeemd, Stanon et al., Waldawer et al., Tute, Hansch and Fujita). The theoretical expectation of the possibility that squalene is an antiviral compound has been confirmed by the in vitro assay where its results testifies that squalene has antiviral activity using the IFN as a reference.

Therefore, the present invention introduces the SQUALENE as antiviral compound specifically for hepatitis C virus administered orally as 500 mg twice/day and 2–3 drops (10–15 mg.) through the nasal membrane three times per day for a period of two to six months depending on the viral load in the patient which could be tested periodically by the polymerase chain reaction {PCR (HCV) RNA} quantitative hepatitis C test.

Therefore, it is the principal object of the invention to introduce the squalene as an antiviral compound for hepatitis C virus.

It is another object of the invention to include other compounds which are structurally related to squalene i.e., any compounds having aliphatic conjugated π bonding, as they might have antiviral activity against hepatitis C virus.

Another object of the invention is the advantage of using squalene, where it is available as squalene soft gel capsules sold in any natural food store for $15/100 capsules, 500 mg. Each, safe vegetable extract and squalene from Shark Liver extract.

It is a further object of the invention to provide a method of treatment of HCV by providing a procedure for administration of the squalene.

Still another object of the invention is to provide improved elements and arrangements thereof in a method and composition for treating hepatitis C for the purposes described which is inexpensive, dependable, not toxic and fully effective in accomplishing its intended purposes.

EXAMPLE

The patient in this case is in the medical profession, was infected by a contaminated syringe on May 21, 1984. He has been diagnosed then as HBV case and received γ-Globulin, and the follow-up showed negative HBV infection. On a late stage, early 1990, the patient start complaining from abdominal pain, liver enlargement, tendency to sleep for a long periods of time, gastric and intestinal discomfort and general weakness in his body. His periodic blood chemistry showed that his alanine aminotransferase (ALT) [normal level is 0–45 u/l] was 137 on January of 1990, 150 on November of 1993 and 139 on January of 1994. At that time he went for explicit diagnostic tests which concluded that the patient had cirrhosis with chronic hepatitis C, portal hypertension with varices and duodenal ulcer. It was prescribed for the patient Omeprizole and Indoral for treatment of ulcer and portal hypertension respectively and an advice for seeking liver transplant was given. The time was against him, where it results in progressively worsening liver inflamation. The herbal treatment was the only alternative for him, Then he found by the analysis of the herbal extract that it contains toxic substances and concluded that squalene was the ingredient that causes the reduction in the viral load. Therefore he switched to squalene treatment. Table 3. Shows the progress of the ALT and the decrease in the virus load as indicated by PCR-RNA quantitative test. Where the ALT is an enzyme located in the liver cells. It leaks out and make their way into the general circulation when liver cells are injured. It is thought to be a specific indicator of liver inflamation.

As noted in Table 3, HCV-PCR-RNA quantitative test taken one month after starting the treatment showed that the Hepatitis C viral load was more than 30,000 copies per ml serum, which is strongly positive. Four month later, the viral load went down to 20,000 copies per ml serum. Four month later, it showed negative HCV. The viral load quantitative test showed undetected HCV since April of 96 until now. Furthermore, the ALT continued to normalize. Another fact is the Alpha fetoprotein was found to be down to 17, lower than the results of 61 on January, 1995. Although the liver cirrhosis remains, complete recovery from ulcers or varices was found, and most importantly, no Hepatitis C virus remained. In 1997 the patient has been diagnosed as having an end stage liver disease secondary to post necrotic cirrhosis and has been listed for liver transplant. After receiving

TABLE 3

| DATE | ALT | PCR-RNA |
|---|---|---|
| ANALYSIS BEFORE START USING THE SQUALENE TREATMENT. | | |
| 1/23/90 | 137 | No PCR-RNA HCV quantitative analysis |
| 11/11/93 | 150 | No PCR-RNA HCV quantitative analysis |
| 1/1/94 | 139 | No PCR-RNA HCV quantitative analysis |
| STARTING THE TREATMENY WITH SQUALENE ON June $1^{st}$. 1995. | | |
| 6/29/95 | 67 | No PCR-RNA HCV quantitative analysis |
| 7/14/95 | 47 | No PCR-RNA HCV quantitative analysis |
| 7/28/95 | 55 | No PCR-RNA HCV quantitative analysis |
| 8/11/95 | 42 | No PCR-RNA HCV quantitative analysis |
| 8/18/95 | — | 30,120 copies/ml serum |

TABLE 3-continued

| DATE | ALT | PCR-RNA | |
|---|---|---|---|
| 9/7/95 | 55 | No PCR-RNA HCV quantitative anaiysis | |
| 10/12/95 | 51 | No PCR-RNA HCV quantitative analysis | |
| 11/22/95 | 50 | No PCR-RNA HCV quantitative analysis | |
| 12/15/95 | — | 19,940 copies/ml serum | |
| 4/15/96 | 53 | <2,000 copies/ml serum | |
| 6/17/96 | 49 | <2,000 copies/ml serum | The Patient continued using |
| 6/10/97 | 40 | <2,000 copies/ml serum | The Squalene. | a liver transplant, the patient continued on testing for HCV-PCR-RNA, with negative results. Usually most of liver transplant recipients who have history of HCV infection, and use IFN as medication, continue to have HCV in their blood stream after receiving a new liver. This is because the HCV hides inside the leucocytes which work as reservoir for the virus. By using the squalene as a medication, the HCV is completely abolished in the blood serum and in the leucocytes as well. This is an advantage of the squalene treatment over the Interferon.

It is to be understood that the present invention is not limited to the embodiment and example described above, but encompasses any and all embodiments within the scope of the claims.

LITERATURE CITED

1. Purcell, R. H. Hepatitis C Virus; historical perspective and current concepts, *FEMS Microbial Rev.* 14, 181–192, (1994).
2. Van der Poel, C. L. Hepatitis C Virus. Epidemiology, transmission and prevention. In Hepatitis C Virus. Current Studies in Hematology and Blood Transfusion, H. W. Reesink ed. (*Baset: Karger*), pp 137–163, (1994).
3. Love, R. A., Parge, H. E., Wickersham, J. A. Hostomsky, Z., Moomaw, E. W. and Hostomska, Z. in Agouron Pharmaceuticals, Inc. & Habuka, N. and Adachi, T. in Japan Tobacco, Inc. (Central Pharmaceutical Research Institute) and University of Tsukuba, Japan (Center for Tskuba Advanced Research Alliance). "The Crystal Structure of Hepatitis C Virus NS3 Proteinease Reaveals a Trypsin-like Fold and Structural Zink Binding Site." (*Cell,* 87, 331–342, (1996).
4. Kim, J. L., Morgenstern, K. A., Lin, C., Fox, T., Dwyer, M. D., Landro, J. A., Chambers, S. P., Markland, W., Lepre, C. A., O'Malley, E. T., Harbeson, S. L., Caron, P. R. and Thompson, J. A. in Vertex Pharmaceuticals, Inc. & Rice, C. M. from Washington University, School of Medicin. "Crystal Structure of Hepatitis C Virus NS3 Protease Domain Complexed with Synthetic NS4A Cofactor Peptide." *Cell,* 87, 343–355, (1996).
5. Alter, M. J., and Maste, E. E. "The Epidemiology of Viral hepatitis in the United States." *Gastroenterol. Clin. North Am.* 23, 437–455. (1994).
6. Choo, Q. L., Kuo, G., Weiner, A. J., Overby, L. R., Bradley, D. W. and Houghton, M. "Isolation of cDNA clone derived from blood-borne non-A, non-B viral hepatitis." *Science,* 244, 359–362, (1989).
7. Iwarson, S. "The natural course of chronic hepatitis." *FEMS Microbial. Rev.* 14, 201–204,(1994).
8. Alter, H. J., Purcell, R. H., Shih, J. W., Melpolder, J. C., Houghton, M., Choo, Q. L., and Kuo, G. "Detection of antibody to hepatitis C virus in prospectively followed transfusion recipients with acute and chronic non-A, non-B hepatitis." *New Engl. J. Med.* 321, 1494–1500, (1989).
9. Kuo, G., Choo, Q. L., Alter, H. J., Redeker, A. G., Purcell, R. H., Miyamura, T., Dienstag, J. L., Alter, M. J., Stevens, C. E., et al. "An assay for circulating antibodies to a major etiologic virus of human non-A, non-B hepatitis." *Science* 244, 362–364, (1989).
10. Renault, P. F., and Hoofnnagle, J. H. "Side effects of alpha interferon." *Semin. Liver Dis.* 9, 273–277, (1989).
11. Statistical data from C&S Clinical Lab. Inc., P.O Box 5269, Englewood, N.J. 07631-5269.
12. John Gerared, "The Herbal or General History of Plants" the complete 1633 edition is revised and enlarged by Thomas Johnson, Dover Publications Inc., Copyright 1975).
13. James Duke, "CRC Handbook of Medicinal Herbs", CRC Press Inc. Dated Jul. 24, 1986, Scientific Library Pat TM Office.
14. Kee Chang Huang, "The Pharmacology of Chinese Herbs", CRC Press Inc., (1993).
15. Schvarcz R.; Ando, Y., Sonnerborg, A. and Weiland, O.; Combination treatment with interferon alfa-2b and ribavirin for chronic hepatitis C in patients who have failed to achieve sustained response to interferon alone: swedish experience. *J Hepatol.* 1995; 23 (Suppl 2): 17–21.
16. Van de Waterbeemd, H. "The History of Drug Research: from Hansch to Present." *Quant. Struct.-Act. Relat.* 11: 200–204, (1992).
17. Van de Waterbeemd, H. "Recent Progress in QSAR-Technology." *Drug Des. Discov.* 9: 227–285, (1993).
18. Stanon, D. T. Murray, W. J. and Jurs, P. C. "Comparison of QSAR and molecular similarity approaches for a structure-activity relationships study of DHFR inhibitors." *Quant. Struct.-Act. Relat.* 12: 239–245, (1993).
19. Woldawer, A. and Erickson, J. W. "Structure-based inhibitors of HIV-1 protease." *Annu. Rev. Biochem.* 62: 543–585, (1993).
20. Tute, M. S. "History and objectives of quantitative drug design. In Hansch, C., Sammes, P. G. and Taylor, J. B. (eds) *Comperhensive Medicinal Chemistry*, Vol. 4, *Quantitative Drug Design,* pp 1–31. Pergamon Press, New York, (1990).
21. Hansch, C. The physicochemical approach to drug design and discovery (QSAR). *Drug Rev. Res.* 1: 267–309. (1981).
22. Hansch, C. On the state of QSAR. *Drug Inf. J.* 18:115–122, (1984).
23. Craig, P. N. QSAR-origins and present status: a historical perspective. *Drug Inf. J.* 18: 123–130, (1984).
24. Fujita T. Application of quantitative structure-activity relationships in drug design. *Acta Pharm. Jugosl.* 37: 43–51, (1987).

I claim:

1. A method of treating a patient infected with hepatitis C virus with squalene using oral ingestion in combination with nasal inhalation, said method comprising concurrently administering to the patient an oral composition comprising a therapeutically effective amount of squalene, and a nasal composition comprising a therapeutically effective amount of squalene is the active ingredient in both of the compositions.

2. The method of claim 1, wherein each dose of the oral composition comprises 500 mg. of squalene, and is administered two times per day.

3. The method of claims 1 or 2, wherein each dose of the nasal composition comprises 10–15 mg. of squalene, and is administered three times per day at two to three drops per administration.

* * * * *